US012636204B2

(12) United States Patent
Bremer et al.

(10) Patent No.: US 12,636,204 B2
(45) Date of Patent: May 26, 2026

(54) DISPOSABLE HYGIENE ABSORBENT PRODUCT

(71) Applicant: Essity Hygiene and Health Aktiebolag, Gothenburg (SE)

(72) Inventors: Christian Bremer, Gothenburg (SE); Stina Lindlöf, Gothenburg (SE); Marcus Rudén, Gothenburg (SE); Peter Rönnberg, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 1372 days.

(21) Appl. No.: 16/623,614

(22) PCT Filed: Jul. 7, 2017

(86) PCT No.: PCT/EP2017/067092
§ 371 (c)(1),
(2) Date: Dec. 17, 2019

(87) PCT Pub. No.: WO2019/007531
PCT Pub. Date: Jan. 10, 2019

(65) Prior Publication Data
US 2020/0214907 A1     Jul. 9, 2020

(51) Int. Cl.
*A61F 13/513*     (2006.01)
*A61F 13/15*     (2006.01)
(Continued)

(52) U.S. Cl.
CPC .. *A61F 13/51394* (2013.01); *A61F 13/51496* (2013.01); *A61F 13/84* (2013.01);
(Continued)

(58) Field of Classification Search
CPC .......... A61F 5/44; A61F 5/453; A61F 13/471; A61F 13/45–4963; A61F 13/51394;
(Continued)

(56) References Cited

U.S. PATENT DOCUMENTS 4,589,877 A     5/1986   Sivilich
4,627,846 A     12/1986  Ternström
(Continued)

FOREIGN PATENT DOCUMENTS

CN     1689542 A     11/2005
CN     101528171 A   9/2009
(Continued)

OTHER PUBLICATIONS

Dictionary.com. Dictionary.com, LLC [online], [retrieved on Apr. 14, 2023]. Retrieved from the Internet <URL: https://www.dictionary.com/browse/integration> (Year: 2016).*
(Continued)

*Primary Examiner* — Leslie R Deak
*Assistant Examiner* — Linnae E. Raymond
(74) *Attorney, Agent, or Firm* — BUCHANAN INGERSOLL & ROONEY PC

(57)     ABSTRACT

A disposable hygiene absorbent product having a liquid-permeable topsheet of a translucent material, a liquid-impermeable backsheet and an absorbent core arranged between the topsheet and the backsheet is disclosed. The absorbent core has a smaller extension than the topsheet and the backsheet and is surrounded by a peripheral edge area which comprises the topsheet and the backsheet. The edge area has an elastic element extending longitudinally following the shape of the core and/or an outermost peripheral edge of the edge area. The backsheet has a different inherent color than the inherent color of the topsheet, the core and the elastic elements, and has a lower L*-value than the topsheet, the core and the elastic elements as measured by a reflectance spectrophotometer. The topsheet is provided with a printed pattern arranged to mask the elastic elements.

17 Claims, 4 Drawing Sheets

(51) Int. Cl.
*A61F 13/514* (2006.01)
*A61F 13/53* (2006.01)
*A61F 13/84* (2006.01)

(52) U.S. Cl.
CPC .................. *A61F 13/15577* (2013.01); *A61F 2013/53016* (2013.01); *A61F 2013/8402* (2013.01)

(58) Field of Classification Search
CPC ...... A61F 13/51496; A61F 2013/15243; A61F 2013/8497; A61F 13/11
See application file for complete search history.

(56) References Cited

U.S. PATENT DOCUMENTS

| | | | |
|---|---|---|---|
| 5,037,417 | A | 8/1991 | Ternström et al. |
| 5,702,381 | A | 12/1997 | Cottenden |
| 6,565,548 | B1 | 5/2003 | Glaug et al. |
| 10,188,558 | B1 | 1/2019 | Martin, Sr. |
| 2002/0042600 | A1 | 4/2002 | Datta et al. |
| 2002/0143316 | A1 | 10/2002 | Sherrod et al. |
| 2003/0225383 | A1 | 12/2003 | Glaug et al. |
| 2004/0059308 | A1 | 3/2004 | Odderson |
| 2005/0228353 | A1 | 10/2005 | Thomas |
| 2007/0005037 | A1 | 1/2007 | Mansfield et al. |
| 2007/0060901 | A1 | 3/2007 | Alletsee |
| 2007/0100308 | A1* | 5/2007 | Miyairi ............. A61F 13/15772 604/385.01 |
| 2007/0233034 | A1 | 10/2007 | Hildeberg et al. |
| 2007/0287982 | A1 | 12/2007 | Lodge |
| 2008/0103472 | A1 | 5/2008 | Lavon |
| 2010/0262111 | A1 | 10/2010 | Lindstrom |
| 2010/0268185 | A1 | 10/2010 | Bergstroem et al. |
| 2011/0092943 | A1* | 4/2011 | Bishop ............. A61F 13/15577 604/385.29 |
| 2011/0172627 | A1* | 7/2011 | Mateo ................... A61F 13/476 604/385.04 |
| 2012/0022487 | A1 | 1/2012 | Akiyama |
| 2012/0150134 | A1 | 6/2012 | Wei et al. |
| 2012/0226249 | A1 | 9/2012 | Prodoehl et al. |
| 2013/0030403 | A1 | 1/2013 | Bosaeus |
| 2013/0096525 | A1 | 4/2013 | Harmannson et al. |
| 2013/0138070 | A1 | 5/2013 | Drevik |
| 2013/0218119 | A1 | 8/2013 | Bergendahl |
| 2014/0066875 | A1 | 3/2014 | Hopkins et al. |
| 2015/0126951 | A1 | 5/2015 | Sharkey |
| 2015/0148769 | A1 | 5/2015 | Johansson et al. |
| 2020/0179181 | A1 | 6/2020 | Ruden et al. |
| 2020/0179182 | A1 | 6/2020 | Ruden et al. |

FOREIGN PATENT DOCUMENTS

| | | | | |
|---|---|---|---|---|
| CN | 101848691 | A | 9/2010 | |
| CN | 101868209 | A | 10/2010 | |
| CN | 102596138 | A | 7/2012 | |
| CN | 102939062 | A | 2/2013 | |
| CN | 103002850 | A | 3/2013 | |
| CN | 103491910 | B | 8/2016 | |
| CO | 05109272 | A | 10/2005 | |
| CO | 07005754 | A | 1/2007 | |
| CZ | 287990 | B6 * | 3/2001 | ......... A61F 13/4755 |
| EP | 1035818 | A1 | 9/2000 | |
| EP | 1 105 079 | B1 | 4/2003 | |
| EP | 1 561 444 | A1 | 8/2005 | |
| EP | 2 110 107 | A1 | 10/2009 | |
| EP | 3047828 | A1 | 7/2016 | |
| GB | 2 436 291 | A | 9/2007 | |
| JP | H06504700 | A | 6/1994 | |
| JP | 3021237 | U | 2/1996 | |
| JP | 2003052729 | A | 2/2003 | |
| JP | 2005-230493 | A | 9/2005 | |
| JP | 2010-131342 | A | 6/2010 | |
| JP | 2011-502730 | A | 1/2011 | |
| JP | 2013-085831 | A | 5/2013 | |
| JP | 5565920 | A | 3/2015 | |
| JP | 2015058325 | A | 3/2015 | |
| KR | 20-2016-004294 | U | 12/2016 | |
| MX | 2008015630 | A | 12/2008 | |
| RU | 2430710 | C1 | 10/2011 | |
| RU | 2529109 | C2 | 9/2014 | |
| RU | 2568570 | C2 | 11/2015 | |
| RU | 2606067 | C2 | 1/2017 | |
| RU | 2624435 | C2 | 7/2017 | |
| WO | 8606620 | A1 | 11/1986 | |
| WO | 92/15269 | A1 | 9/1992 | |
| WO | 9531164 | A1 | 11/1995 | |
| WO | 00/10495 | A | 3/2000 | |
| WO | 2009067058 | A1 | 5/2009 | |
| WO | 2010/071517 | A1 | 6/2010 | |
| WO | 2011/037502 | A1 | 3/2011 | |
| WO | 2011045685 | A2 | 4/2011 | |
| WO | 2011162652 | A1 | 12/2011 | |
| WO | 2011162658 | A1 | 12/2011 | |
| WO | WO-2011162657 | A1 * | 12/2011 | .......... A61F 13/5611 |

OTHER PUBLICATIONS

Sappi. Defining and Communicating Color: The CIELAB System. Sappi Fine Paper North America, [online], [retrieved on Feb. 12, 2024]. Retrieved from the Internet <URL: https://cdn-s3.sappi.com/s3fs-public/sappietc/Defining%20and%20Communicating%20Color.pdf> (Year: 2013).*

Defining and Communicating Color: The CIELAB System. Sappi Fine Paper North America (2013), [retrieved on Sep. 19, 2022]. Retrieved from the Internet <URL: chrome-extension://efaidnbmnnnibpcajpcglclefindmkaj/https://cdn-s3.sappi.com/s3fs-public/sappietc/Defining%20and%20Communicating%20Color.pdf> (Year: 2013).*

Office Action (Notification of the Second Office Action) issued on Nov. 23, 2021 by the National Intellectual Property Administration (CNIPA) of the People's Republic of China in corresponding Chinese Patent Application No. 201780091843.9, and an English Translation of the Office Action. (19 pages).

Office Action (Notification of the First Office Action) issued on Mar. 26, 2021 by the China National Intellectual Property Administration (CNIPA) of the People's Republic of China in corresponding Chinese Patent Application No. 201780091843.9, and an English Translation of the Office Action. (23 pages).

International Preliminary Report on Patentability for International Application No. PCT/EP2017/067092, dated Sep. 5, 2019, 7 pages.

International Search Report and Written Opinion for International Application PCT/EP2017/067092, dated Feb. 8, 2018, 10 pages.

Office Action No. 14509 issued on Sep. 10, 2021, by the Colombian Patent Office in Colombian Patent Application No. NC2019/0014505 and an English Translation of the Office Action. (18 pages).

Notice of Allowance (Decision to Grant/ A Patent for Invention) issued on Sep. 10, 2020, by the Federal Service for Intellectual property in Russian Patent Application No. 2019139673/28(078097) and an English Translation of the Notice of Allowance. (17 pages).

Third Office Action dated May 9, 2022, issued in the corresponding Chinese Patent Application No. 201780091843.9, 8 pages including 4 pages English Translation.

International Search Report and Written Opinion for International Application No. PCT/EP2017/067102, dated Dec. 1, 2017. (8 pages).

Office Action (Notification of the First Office Action) issued on Nov. 26, 2019, by the State Intellectual Property Office of the People's Republic of China in corresponding Chinese Patent Application No. 201780091225.4 and an English translation of the Office Action. (23 pages).

Office Action (Decision on Grant) issued on May 13, 2020 by the Federal Service for Intellectual Property in Russian Patent Application No. 2019139401/(077480) and an English translation of the Office Action. (22 pages).

(56)  References Cited

OTHER PUBLICATIONS

International Search Report and Written Opinion for International Patent Application No. PCT/EP2017/064538, dated Dec. 4, 2017. (9 pages).

International Preliminary Report on Patentability for International Patent Application No. PCT/EP2017/064538, dated Oct. 2, 2019. (6 pages).

Office Action issued on Sep. 17, 2020, by the U.S. Patent and Trademark Office in related U.S. Appl. No. 16/618,624. (17 pages).

Office Action issued on Sep. 17, 2020, by the U.S. Patent and Trademark Office in related U.S. Appl. No. 16/618,636. (14 pages).

Office Action issued on Apr. 1, 2020, by the Australian Government/ IP Australia in corresponding Australian Patent Application No. 2017422277. (3 pages).

Office Action issued on Jun. 4, 2020, by the Federal Service for Intellectual Property in Russian Patent Application No. 2019139673(078097) and an English Translation of the Office Action. (21 pages).

Office Action (Communication pursuant to Article 94(3) EPC) issued by the European Patent Office in corresponding European Patent Application No. 17 742 957.8-1118, dated Jun. 9, 2023 (4 pages).

Office Action (Notice of Reasons for Rejection) issued on Jan. 12, 2021, by the Japanese Patent Office in corresponding Japanese Patent Application No. 2020-500118, and an English Translation of the Office Action. (15 pages).

* cited by examiner

DISPOSABLE HYGIENE ABSORBENT PRODUCT

CROSS REFERENCE TO RELATED APPLICATIONS

This is a U.S. National Phase application of PCT/EP2017/067092, filed Jul. 7, 2017, the disclosure of which is incorporated herein by reference in its entirety for all purposes.

TECHNICAL FIELD

The present invention relates to a disposable hygiene absorbent product and to a process for the production of a disposable hygiene product as defined in the appended claims

BACKGROUND

Disposable hygiene absorbent products are well known in the art and can be provided for example in the form of incontinence guards, which can be aimed for female or male users, baby diapers, sanitary napkins and panty liners. An example of a known male incontinence guard is shown in WO86/06620.

Disposable hygiene products need to have good absorptive properties and comfort and they need to provide a sense of leakage security and good fit for a user. Various designs and methods have been employed in the products so that they can follow the contours of the user's body well and so that they do not move out of place during use. Therefore, the products may contain elastic bands, which together with the shape of the product provide good fit to the anatomy of the wearer and thus improve the leakage security.

The skin of the user is often very sensitive in proximity to the area where the hygiene product is placed during use. Therefore, it is important that the product edges and elastic elements do not chafe the skin and development work has been done to reduce chafing and thus to improve product comfort. However, despite the efforts to improve the elastic materials there is still a risk that elastic elements may appear uncomfortable to the user even before the use of the products. Therefore, there is a need to reduce the risk that the user will discard the use of the products due to the fear of uncomfortable feeling during use, while the leakage security properties are maintained or even improved.

SUMMARY

In view of the problem above, it has been noted that there is a need to improve the visual appearance of the products. In general it has been noted that the product needs to include elastic elements, but the appearance of the product with visible elastic elements can give an impression of being an irritation to the skin in the crotch area. The problem appears to be greater in hygiene products which comprise a colored backsheet material which faces underwear of the user. The color of the backsheet is often darker than the color of the topsheet and a core of the product, e.g. grey, to better adapt to the color of the underwear. In contrast, the elastic elements are often opaque and have a light color, e.g. nearly white, and thus close to the color of the topsheet material and the core. Therefore, there is a large contrast between the dark color of the backsheet material and the elastic elements, which both are visible through the topsheet material, which is usually translucent. Thus, a problem of providing a hygiene product with improved visual appearance also from the topsheet side of the product in combination with good fit and leakage security has been realized.

Therefore, it is an objective of the present invention to provide a disposable hygiene product which has good leakage security, is comfortable to use and has improved visual appearance. It is an objective to improve the visual appearance of the product so that the risk that the user discards the use of the product due to a fear that the product will be uncomfortable during the use is reduced. Thus, it is an objective to increase the user's confidence in the product.

The objectives above are attained by the disposable hygiene product and a production process thereof as defined in the appended claims. Especially, it has been noted that a considerably improved appearance, while the comfort and fit of the product are good or even improved, can be provided if the product comprises a printed pattern which is arranged to mask the elastic elements. Thus, the present disclosure relates to a disposable hygiene absorbent product comprising a liquid-permeable topsheet of a translucent material, a liquid-impermeable backsheet and an absorbent core arranged between the topsheet and the backsheet. The absorbent product has a longitudinally extending centre line extending centrally through the absorbent product and the absorbent product extends in a flattened-out configuration in a longitudinal direction and in a transversal direction. The topsheet and the backsheet have substantially the same extension and the absorbent core has a smaller extension than the topsheet and the backsheet in both the longitudinal and the transversal direction. The core is surrounded with a peripheral edge area which comprises the topsheet and the backsheet. The edge area comprises over at least a portion of the length on respective side of the centre line an elastic element extending longitudinally in the direction following the shape of the core and/or an outermost peripheral edge of the edge area. The backsheet has a different inherent color than the inherent color of the topsheet, the core and the elastic elements, and has a lower L\*-value than the topsheet, the core and the elastic elements measured by a reflectance spectrophotometer. The topsheet is provided with a printed pattern arranged to mask the elastic elements. By the printed pattern being arranged to mask the elastic elements is meant that the printed pattern is arranged to at least decrease the visibility of the elastic elements, but may also completely mask them. By providing the printed pattern so that it masks the elastic elements, the visual appearance of the product is improved. The measurement by means of a reflectance spectrophotometer is described later on in the application in more detail, and reference is herein made to the detailed description.

The printed pattern usually covers at least the elastic elements. Preferably, in an embodiment, the printed pattern additionally covers areas free of the elastic elements in the peripheral edge area, and optionally at least a core peripheral portion covering a core edge. In this way, the visual appearance may be further improved and it will be possible to indicate the absorptive area of the core in an easy manner.

According to certain embodiments, the color difference delta ($1k$) E between the printed pattern in the edge area comprising the elastic elements and the printed pattern in the edge area free of the elastic elements is less than 10, suitably less than 8 and preferably less than 6, more preferably less than 4 and most preferably less than 2, measured by means of a reflectance spectrophotometer, from the topsheet side of the product. By having delta E less than 10, sufficient masking of the elastic elements is obtained. The lower the delta E value, the smaller is the experienced color difference:

when the value is below 2, the color difference is not visible or nearly not visible to the human eye.

According to one aspect, in certain embodiments, the color difference delta E between the printed pattern in the edge area comprising the elastic elements and the printed pattern in the edge area free of elastic elements is less than, preferably at least 50% less than, more preferably at least 60% less than, the color difference delta E between the printed pattern in the edge area comprising the elastic elements and a printed pattern free area of the topsheet covering the core, measured by means of a reflectance spectrophotometer from the topsheet side of the product. Thus, the color difference is larger between the non-printed and printed regions in the product than between the different printed regions on the edge area of the product. Thereby, the color difference between the printed pattern in the edge area comprising the elastic elements and the printed pattern in the edge area free of elastic elements may appear small or non-visible for the human eye.

Also, according to a further aspect, in certain embodiments, the color difference delta E and/or delta L*-value between the printed pattern in the edge area free from elastic elements and a printed pattern free area of the topsheet covering the core, measured by means of a reflectance spectrophotometer from the topsheet side of the product, is at least 10, preferably at least 15. The larger the difference, the smaller the difference in the edge area between the elastic element-containing and elastic element-free areas appears.

Suitably, the printed pattern extends symmetrically from the outermost peripheral edge of the edge area towards a centre point of the product over the core edge such that at least 50% of the total area of the topsheet covering the core is free of the printed pattern. In this way, it may be for example easily indicated how the product can be positioned during use.

According to one variant of the invention, the printed pattern comprises or consists of a pattern having the same color but different chroma and/or lightness than the backsheet. Alternatively, the printed pattern may comprise or consist of a pattern having different color, chroma and/or lightness than the backsheet. The type of the pattern is thus flexible, as long as the masking effect is provided.

The backsheet, topsheet and elastic elements arranged between the topsheet and the backsheet are suitably joined together along the edge area by means of adhesive. Adhesives, which can for example be applied by means or spraying or with other coating means, are commonly used in hygiene products and provide a robust construction for the products with improved comfort. The adhesives are usually colorless or nearly colorless in dry condition in the product.

The disposable hygiene product may have different shapes. According to a variant the product has a centre line which divides the product into mirror imaged first and second longitudinal portions which are symmetrical in respect of the centre line. In this way a product which is easy to position is obtained.

According to an embodiment, the product has a head portion, an intermediate portion and a rear portion. The head portion comprises in each longitudinal portion an arch-shaped edge portion having two opposing outermost first transition points in the transverse direction in the outermost edge of the edge portion, wherein a broadest first product width extends between said outermost first transition points. The head portion transitions into the intermediate product portion at said first transition points. The edge portion in the intermediate product portion tapers towards a central end point in the rear portion of the product and the intermediate portion transitions to the rear portion at rear portion transition points longitudinally distanced from the first transition points and the central end point. In this way a product having a shape resembling a triangular shape can be provided, which is especially suitable for male incontinence pads or pantyliners. The shape could also resemble a quadrilateral shape, which may also have a broader head portion tapering towards rear. Preferably, in an embodiment, the elastic elements extend in the edge area in the first and second longitudinal portions within the intermediate rear portion and are inclined in respect of the centre line. In this way a bowl shape can be provided to a product having a tapering shape.

According to a further variant the shape of the product may resemble an hourglass-shape. Such product may also comprise a head portion, a centrally located intermediate portion and a rear portion, wherein the elastic elements extend in the first and second longitudinal portions in the intermediate portion. Thus, the shape of the product can be flexible.

The elastic elements suitably comprise or consist of foam elastics or laminate film elastics. Preferably, in an embodiment, the elastic elements are foam elastics, which are skin friendly.

The topsheet may comprise a further printed pattern distanced from the printed pattern comprised in the edge area. In this way the visual appearance of the product can be further improved and e.g. indicators in respect of different functionalities in the product can be added.

The present disclosure also relates to a process for the production of a disposable hygiene product comprising:

providing a layer of topsheet material, a layer of backsheet material and an absorbent material for an absorbent core and forming the core;

providing a material for elastic elements (10; 10')

feeding the elastic elements in a pre-tensioned condition such that they are arranged between the layer of the topsheet material and the backsheet material, and cutting the elements to a predetermined length;

feeding the absorbent core between the topsheet layer and the backsheet layer;

attaching the topsheet layer, the backsheet layer and the elastic elements together along a peripheral edge area by means of attachment means, preferably adhesive according to an embodiment;

synchronizing a printed pattern with the placement of the absorbent core so that the printed pattern masks the elastic elements.

Further objectives, features and advantages of the present disposable hygiene product and the method for the manufacture of the product are described in the detailed description below with reference to the appended drawings.

DETAILED DESCRIPTION OF PARTICULAR EMBODIMENTS

The present disposable hygiene product is an absorbent product aimed for personal hygiene and may be for example a sanitary towel, a panty liner, an incontinence pad or guard or a diaper. Such products are commonly used for acquisition and storage of bodily exudates such as urine, faeces or menstrual fluid. The absorbent product is disposable, which means that it is intended to be used only once and disposed thereafter, rather than being cleaned and re-used. The absorbent product may suitably be an incontinence guard, preferably, according to an embodiment, a male incontinence guard for which the design of the product is especially suitable.

Figure 1:
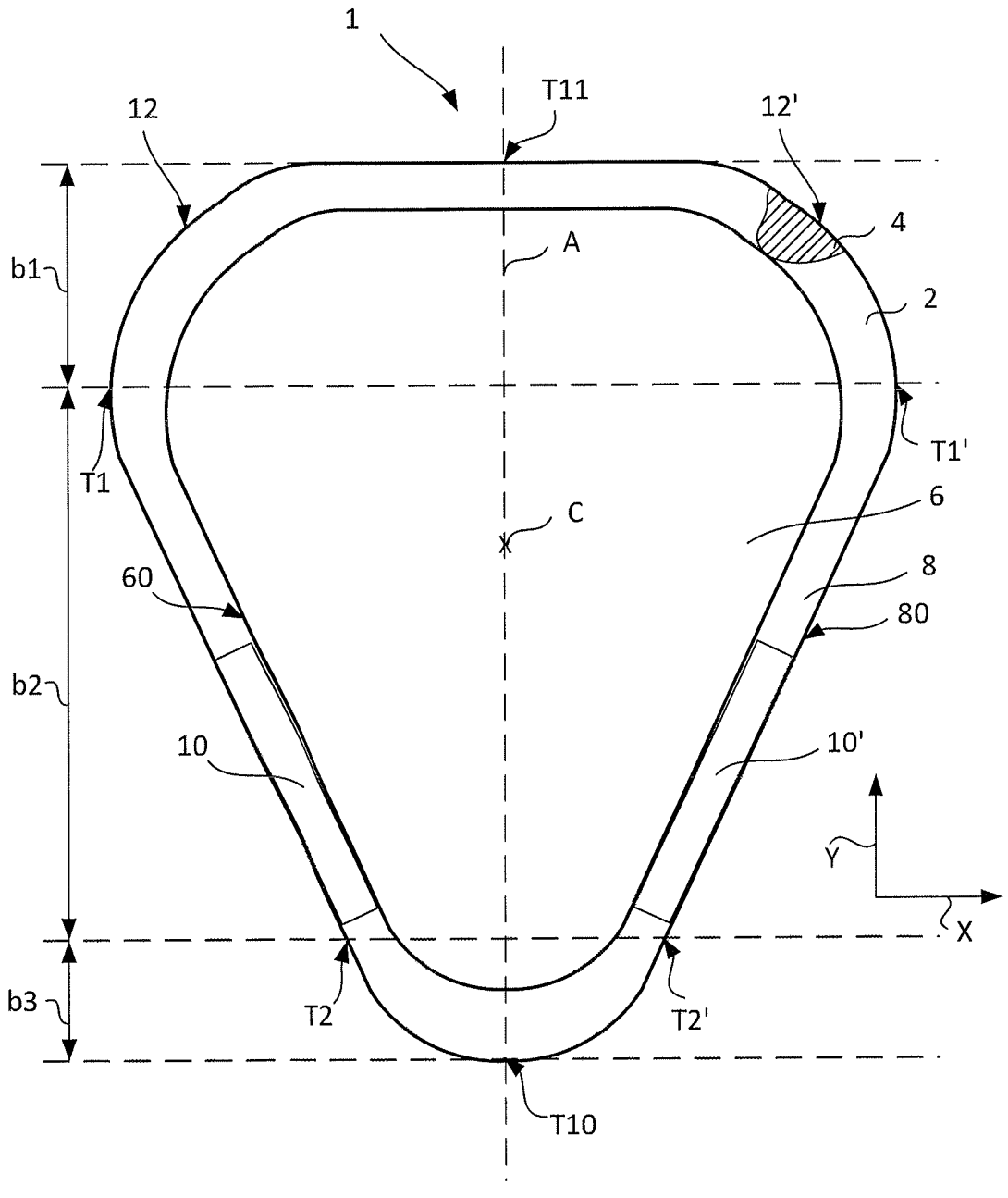
FIG. 1 shows schematically a top view of an example disposable hygiene product comprising elastic elements.
Figure 2:
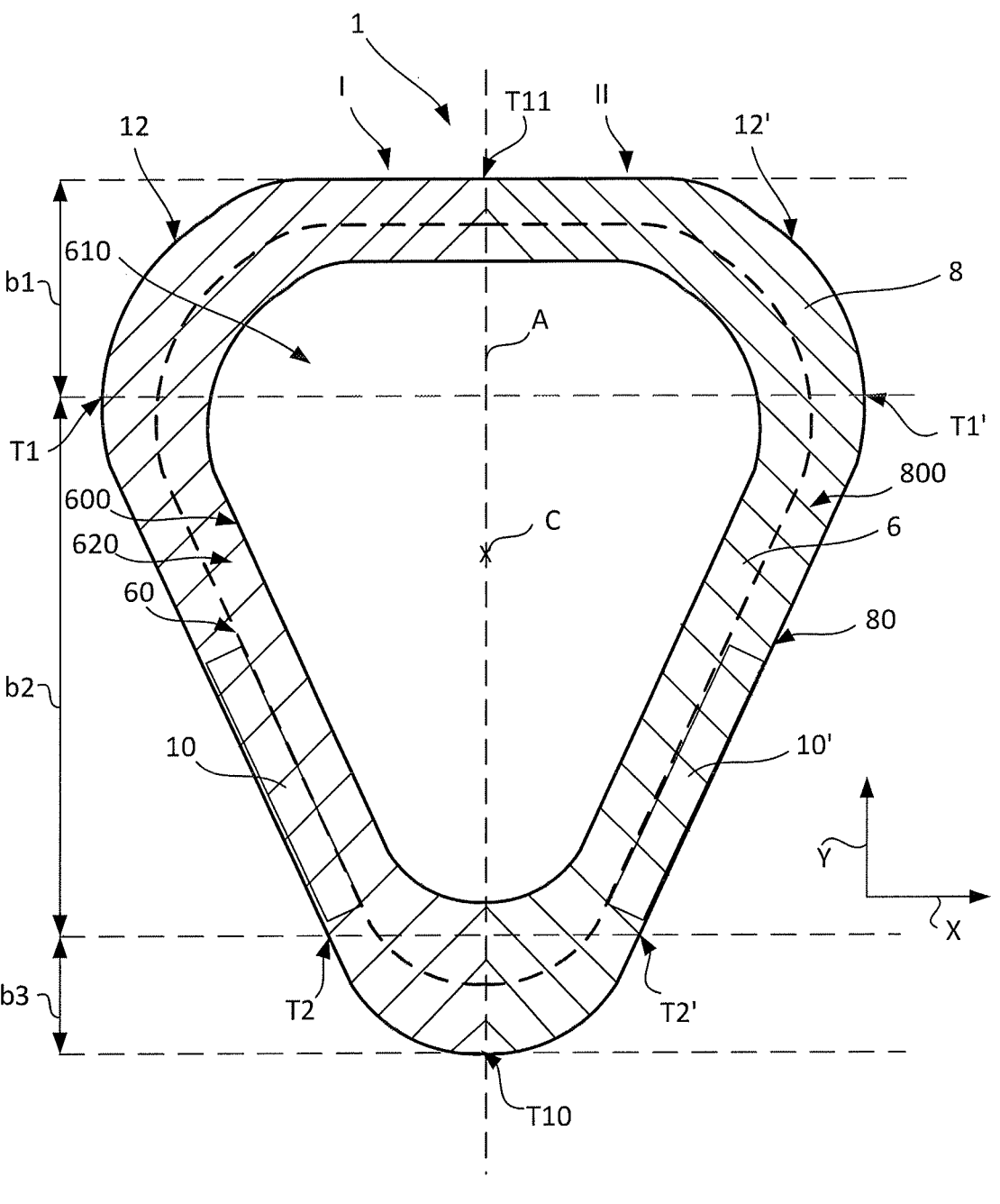
FIG. 2 shows a top view of the product shown in FIG. 1 and comprising a printed pattern that masks the elastic elements.
Figure 3:
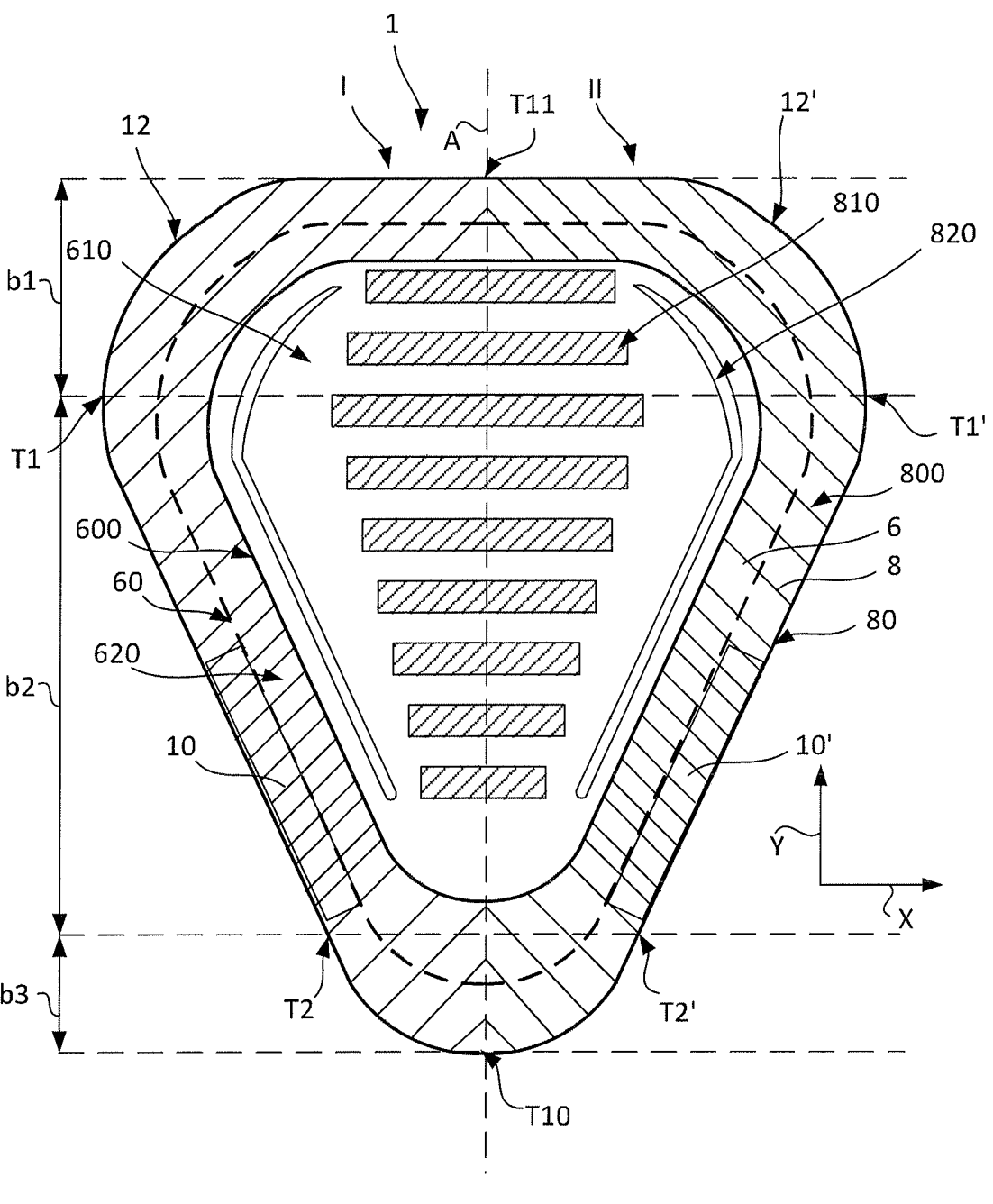
FIG. 3 shows a top view of the product shown in FIG. 1 and comprising a printed pattern that masks the elastic elements and additional printed patterns.
Figure 4:
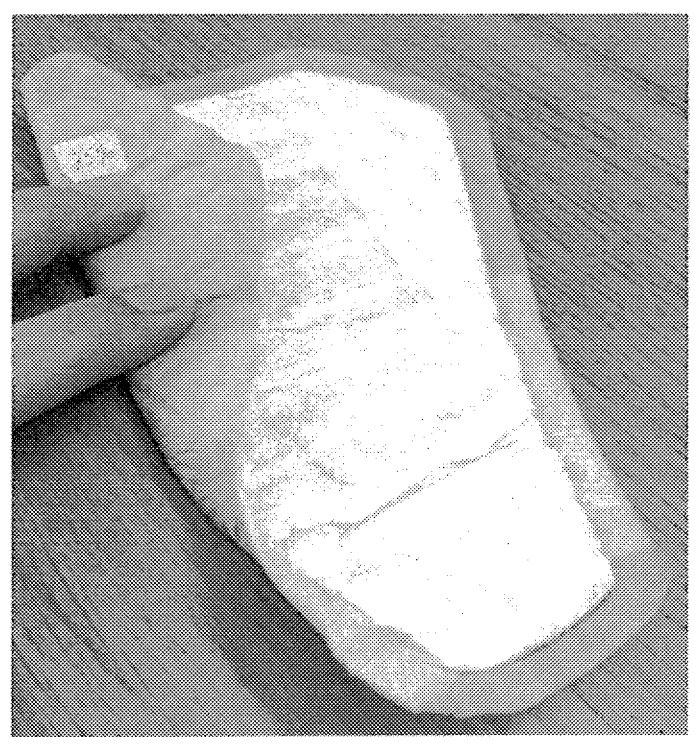
FIG. 4 shows a photograph of an absorbent product with dark backsheet and visible elastic elements.

Reference is made to the appended drawings FIG. 1, FIG. 2 and FIG. 3. The disposable hygiene product 1 of the present disclosure comprises a liquid-permeable topsheet 2 of a translucent material, a liquid-impermeable backsheet 4 and an absorbent core 6 arranged between the topsheet 2 and the backsheet 4. The topsheet 2 lies in direct contact with the wearer's body, and should therefore be soft, comfortable and liquid-permeable. The absorbent product extends in a flattened-out configuration in a longitudinal direction Y and in a transversal direction X. The topsheet 2 and the backsheet 4 have substantially the same extension in the product and the absorbent core 6 has a smaller extension than the topsheet 2 and the backsheet 4 in both the longitudinal and the transversal direction. Thereby, the core 6 is surrounded by a peripheral edge area 8 which comprises the topsheet 2 and the backsheet 4, where they are attached together. The edge area 8 further comprises over at least a portion of the length on respective side of the product in respect of the centre line A an elastic element 10; 10', which extends longitudinally in the direction following the shape of the core 6 and/or an outermost peripheral edge 80 of the edge area 8. The elastic elements 10, 10' are provided to improve the fit of the product to the anatomy of the user. The elastic elements can basically provide a bowl-shape for the absorbent product, which conforms to the body of the user, whereby also the leakage security is improved. Generally, the elastic elements may be provided in the form of bands of elastic foam, elasticized film or elastic laminate or alternatively elastic strands. To improve the comfort of the product the elastic elements can be provided in the form of bands of elastic foam.

The topsheet 2 and the backsheet 4 can be joined together by any suitable means, for example by means of adhesive. Other methods include welding e.g. by means of ultrasound or laser, mechanical joining e.g. by means of embossing or compression or thermal bonding. The peripheral edge area 8 surrounds the core 6 along the whole perimeter of the core 6. The width of peripheral edge area 8, i.e. the extension of the area from an outer peripheral edge 80 of the product 1 inwards towards the core 6 of the product 1, the width being perpendicular to the longitudinal extension of the peripheral edge 80, suitably towards a centre point C, can be from 5 mm to 30 mm. The centre point C is a point located on the centre line A at a middle point between a front central point T11 and rear central point T10.

The topsheet 2 can comprise a nonwoven material, e.g. spunbond, meltblown, carded, hydroentangled, wetlaid etc. Suitable nonwoven materials can be composed of natural fibres, such as wood pulp or cotton fibres, manmade fibres, such as polyester, polyethylene, polypropylene, viscose etc. or from a mixture of natural and man-made fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, e.g. urine. The topsheet material has an inherent color of white or close to white, and has a higher L*-value according to CIELab color scale and measured by means of a reflectance spectrometer than the backsheet.

The backsheet 4 lies in contact with the wearer's garments, and is liquid-impermeable. The backsheet 4 refers to the liquid impervious material forming the outer cover of the absorbent product 1. The backsheet can comprise a thin plastic film, e.g. a polyethylene or polypropylene film, a nonwoven material coated with a liquid impervious material, a hydrophobic nonwoven material, which resists liquid penetration, or a laminate of a plastic film and a nonwoven material. Other laminate materials which are suitable for use as the backsheet are laminates comprising a nonwoven material. The backsheet material may be breathable so as to allow vapour to escape from the absorbent core, while still preventing liquids from passing there through. Examples of breathable backsheet materials are porous polymeric films, nonwoven laminates of spunbond and meltblown layers and laminates of porous polymeric films and nonwoven materials. Preferably, in an embodiment, the backsheet 4 comprises nonwoven material on at least the garment-facing surface thereof. According to the present disclosure, the backsheet 4 has a different inherent color than the inherent color of the topsheet 2 and the core 6. Preferably, in an embodiment, the backsheet material has a lower L*-value than the topsheet 2, the core 6 and the elastic elements 10; 10'.

The absorbent core is the absorbent structure of the product which acquires and stores bodily fluids. The absorbent core may be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, poly-acrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked according to an embodiment, to render the material substantially water insoluble. In an embodiment, preferred superabsorbent materials are further surface cross-linked so that the outer surface or shell of the superabsorbent product, fibre, flake, sphere, etc. possesses a higher crosslink density than the inner portion of the superabsorbent. The superabsorbent materials may be in any form suitable for use in absorbent composites including products, fibres, flakes, spheres, and the like. A high absorption capacity is provided by the use of high amounts of superabsorbent material. Thin absorbent cores which are common in for example sanitary napkins, baby diapers and incontinence guards, often comprise a compressed, mixed or layered structure of cellulosic fluff pulp and superabsorbent polymers. The size and absorbent capacity of the absorbent core may be varied to suit different product types, such as incontinence guards for adult incontinent persons or panty liners.

Generally, the core can be of unitary construction, whereby for example the manufacturing process can be simplified. The phrase "unitary construction" in the present context is intended to mean that the absorbent core is constructed from essentially one type of material, this being essentially the same material, or essentially the same combination of two or more materials throughout the absorbent core. Variations in density and concentration of the material occur, but these are limited to those which may be obtained without incorporation of regions which have been formed separately and then physically joined to each other. For example, when the absorbent core comprises a matrix of hydrophilic fibres and superabsorbent material as described above, the relative concentrations of superabsorbent material and fibres may be different in different parts of the core. However, the absorbent core of unitary construction does not comprise layers or laminates of different composition. Likewise, variations in the density or concentration of various components across the longitudinal direction, the transverse direction or the thickness direction of the absorbent core are acceptable, yet the core should not comprise areas or layers of different composition which are formed separately and later joined together. Examples of methods for production of the absorbent core will be described below.

The absorbent product may further include a liquid acquisition sheet, which acts as a liquid distribution layer. The liquid acquisition sheet is located between the topsheet and the core and is suitably placed on top of the absorbent core. The liquid acquisition sheet is adapted to quickly receive and temporarily store discharged liquid before it is absorbed by the absorbent core. Such acquisition distribution layers may be composed of for example airlaid nonwoven, spunlace nonwoven, high loft nonwoven or foam materials, which are well known in the art. The nonwoven material may be hydrophilic. A hydrophilic material may be obtained by adding a surfactant.

According to the present disclosure, the topsheet is provided with a printed pattern 800 as schematically shown in FIGS. 2 and 3. The printed pattern 800 is arranged to mask the elastic elements 10; 10'. The printed pattern 800 comprises printed areas of certain color, also referred to as hue. Examples of colors are e.g. white, black, red, blue, violet, orange, yellow, green and indigo, as well as any declination thereof or mixture thereof. The printed pattern 800 covers at least the elastic elements 10; 10', but, in an embodiment, preferably covers also areas free of elastic elements 10; 10' in the peripheral edge area 8. Further, the printed pattern may cover at least a core peripheral portion 620 covering a core edge 60. The core peripheral portion 620 is an area extending from the core peripheral edge 60 inwards towards the centre point C of the product, and can have a width, i.e. an extension perpendicular to the longitudinal extension of the edge 60, from 5 mm to 30 mm, but is not limited thereto.

The printed pattern 800 may comprise or consist of a single continuous colored region which comprises at least one of the basic printing colors C (cyan), M (magenta), Y (yellow) and K (black), or comprises a combination of the basic printing colors. Alternatively or additionally, the printed pattern 800 comprises areas of different density or intensity. The printed pattern may comprise one or more sub-patterns, which together form an impression of a continuous, homogenous pattern. For example, the pattern may comprise a plurality of small items of a specific geometrical shape, e.g. a rectangle, circle or triangle. The size of each individual item can be from 0.02 $mm^2$ to e.g. 1 $mm^2$, but is not limited thereto, and there may be e.g. from 10-100 equally distributed items per 1 $cm^2$ to provide an impression of a continuous pattern. Alternatively, the printed pattern may be a single continuous tone, which may have different densities and can be e.g. denser at the area covering the elastic elements.

The colors can be measured by means of a reflectance spectrophotometer measuring the L*, a* and b* values of the color. The L*, a* and b* values to define the difference in color of the printed pattern 800 compared to other regions in the absorbent product 1 are measured from the body facing surface of the topsheet in the assembled product, unless otherwise indicated. The inherent L*, a*, and b* values of a component of the absorbent hygiene products, such as of the topsheet or the backsheet respectively, are measured from the indicated surface of that material.

The difference in color is calculated using the L*, a*, and b* values by the equation:

$$\text{Delta}(\Delta)E=[(L^*_X-L^*_Y)^2+(a^*_X-a^*_Y)^2+(b^*_X-b^*_Y)^2]^{1/2} \tag{I}$$

The 'X' in the equation (I) represents a first measuring point, and may for example represent a point in the peripheral edge area 8, which comprises the elastic bands (10; 10') and 'Y' may represent the color of a point in the peripheral edge area 8, which is free of the elastic elements (10; 10'). Thus X and Y should not be the same two points of measurement at the same time. Where more than two colors are used, the 'X' and 'Y' values alternately include points of measurement in them also. The key to the ΔE calculation herein is that the 'X' and 'Y' values should not stem from the same measured point on the viewing surface.

In the context of the present specification, color, i.e. L*, a* and b* values, were measured using a Techkon Spetro-Dens Premium measurement device obtainable from Techkon of Danvers, MA, US. Measurements were performed at an ambient temperature of between 23±1° C. and a relative humidity of 50±10%. The measured product was acclimatized at these measurement conditions for at least 24 h prior to measurement. The spectrophotometer was set to the CIELab color scale and settings D50/2°/noPOL/ABS, according to the User's manual, and equipped with a 1.5 mm or 3 mm aperture. Either the 3 or 1.5 mm aperture may be used, as long as all measurements to be compared with each other are made using the same aperture. The aperture is preferably chosen, in an embodiment, such that the region, in which the color is to be measured, is larger than the aperture.

In the measurements reported in the present disclosure, a 3 mm aperture was used. The spectrophotometer is calibrated prior to sample analysis utilizing the white reference tiles supplied from the vendor with the instrument. Calibration is done according to the manufacturer's instructions as set forth in User's manual. Any sample point on the absorbent product containing the imparted color to be analyzed can be selected.

The object of measurement is placed on top of a stack of three sheets of white standard office printing paper (Everyday paper 80 $g/m^3$ from Office Depot, Sweden), which in turn is placed on a bench of white, opaque material. The L*-value measured on the top of the stack was 96±1. The object of measurement is to be in a substantially flat condition and free of wrinkles. For each reported value, ten (10) readings of color are conducted at different locations. If possible (e.g., the size of the imparted color on the element in question does not limit the ability to have ten discretely different, non-overlapping sample points), each of the readings is to be performed at a substantially different region so that no two sample points overlap. If the size of the imparted colored region requires overlapping of sample points, the samples should be taken with the sample points selected to minimize overlap between any two sample points. The readings are averaged to yield the reported L*, a*, and b* values for a specified color. It is foreseen that any equipment suitable to measure L*, a* and b* values according to the CIELab color scale on the type of material used in absorbent hygiene products could be used to obtain the values disclosed in the present application.

In the context of the present disclosure, a difference is made between an inherent color (L* or a* or b* value) of a material and the color in the assembled absorbent hygiene product. An inherent color is measured on the material per se, while the corresponding value for the absorbent hygiene product is measured on the assembled product. Unless a color is indicated to represent the inherent color, it is to be understood that the value is measured on the assembled absorbent hygiene product.

It is to be understood in the context of the present disclosure that the color measurements are performed according to the color measurement method disclosed herein.

The topsheet is made of a translucent material, i.e. it permits light to pass through. The topsheet material may have an inherent L*-value that is at least 80, such as at least 85, for example at least 90, and at most 96. The topsheet is provided with the printed pattern 800 arranged to mask the elastic elements 10; 10'. In the context of the present disclosure, the printed pattern 800 may comprise or consist of a pattern having the same color but different chroma and/or lightness than the backsheet 4 and is preferably substantially homogenous, in an embodiment. By chroma is meant the intensity or purity of a color. By lightness is meant the relative degree of black and white mixed with a given color. Alternatively, the printed pattern 800 may comprise or consist of a pattern having different color, chroma and/or lightness than the backsheet 4. Still, the pattern 800 is preferably substantially continuous and homogenous, in an embodiment. However, the topsheet may comprise at least one further printed pattern, which is distanced from the printed pattern 800 comprised in the edge area 8. For example, as illustrated in FIG. 3, the absorbent product may comprise a printed pattern 810 comprising a plurality of individual elements having a longer transversal extension than longitudinal extension to indicate an absorption zone or the product. A further pattern 820 may be provided symmetrically on respective side of the centre line to indicate the boundaries of the absorption zone, and thus give information to the user of optimal placement of the product.

In the context of the present disclosure, according to certain embodiments, the color difference delta E between the printed pattern 800 in the edge area 8 comprising the elastic elements 10; 10' and the printed pattern in the edge area 8 free of the elastic elements is less than 10, suitably 8 and preferably 6, more preferably less than 4 and most preferably less than 2, measured by means of a reflectance spectrophotometer as described above from the topsheet side of the product 1. In this way, the color difference is sufficiently low so that the printed pattern 800 is able to decrease the visibility of the elastic elements. This means that an impression of continuous and homogenous edge area 8 is given to the user.

The printed pattern 800 suitably extends symmetrically from the outermost peripheral edge 80 of the product edge area 8 towards the centre point C of the product 1 over the core edge 60. However, suitably at least 50%, and up to 100% of the total area of the topsheet 2 covering the core 6 is free of the printed pattern 800. Generally however the printed pattern 800 may cover other regions of the topsheet than the edge region 8 and may cover from 5% up to about 50% of the total area of the topsheet 2. If the topsheet comprises at least one of the additional printed patterns 810 and 820, the total area covered by printed patterns may be up to 90% of the total area of the topsheet 2 in the product. The topsheet area free of a printed pattern is located above the core 6 and is indicated by reference sign 610 in FIGS. 2 and 3.

The backsheet may be opaque or it may be translucent. At least the side of the backsheet that faces the topsheet is provided with a color having an inherent L*-value that is significantly lower than the inherent L*-value of the topsheet, and lower than the inherent L*-value of topsheet facing surface of the absorbent core. This means that the backsheet is darker than the topsheet. The color on the topsheet-facing side of the backsheet may be substantially uniform, at least within the area of the backsheet that will be part of the edge area of the absorbent hygiene product when assembled.

In the context of the present disclosure, according to certain embodiments, an area having "substantially uniform color" is to be interpreted as the color difference ($\Delta E$) between any two regions of the same area is at most 2, preferably at most 1. Alternatively, the color on the topsheet-facing side of the backsheet may vary over the surface, so long as that portion of the topsheet-facing side of the backsheet that has the highest inherent L*-value, has an inherent L*-value that is lower than the inherent L*-value of the topsheet facing side of the absorbent core.

The color may be applied to the backsheet in any manner known to the person skilled in the art, resulting in the desired color. For example, the backsheet may be of, or comprise, a material having an inherent color, or may be subjected to a print process to provide the backsheet color. In some embodiments, the backsheet comprises, or consist of, a plastic film, which may be made from a pigmented plastic material.

Due to the translucency of the topsheet, the side of the backsheet that faces the topsheet, will at least partly be visible through the translucent topsheet and therefore make the edge area 8 free of the elastic elements 10; 10' to appear darker. For this reason the elastic elements 10; 10' appear more clearly in products having colored backsheet. Also, the absorbent core 6 and/or other layers located between the absorbent core 6 and the topsheet 2 are usually selected such that they have a higher L*-value, i.e. appear lighter or brighter, than the edge area 8. The L*-value of the absorbent core 6 and the topsheet 2 is usually at least 75, at least 78, at least 80, at least 83, at least 87 or at least 90, and is at most 100 or at most 95.

The difference between L*-value of the printed pattern free area 610 of the topsheet 2 above the core 6 and the L*-value of the edge area free of elastic elements or comprising the elastic elements may be up to 100% of the L*-value of the printed pattern free area 610, given that the lowest possible L*-value of the edge area 8 free of elastic elements or comprising the elastic elements is 0, i.e. black.

However, the printed pattern is usually not completely black, and therefore, according to certain embodiments, the L*-value is suitably at least 5, preferably at least 7, more preferably at least 10, and even more preferably at least 20, and at most 80, such as at most 60, for example at most 50.

The color difference delta E between the printed pattern 800 in the edge area 8 comprising the elastic elements 10, 10' and the printed pattern 800 in the edge area 8 free of elastic elements 10; 10' is less than the color difference delta E between the printed pattern in the edge area 8 comprising the elastic elements 10, 10' and a printed pattern free area 610 of the topsheet 2 covering the core 6, measured by means of a reflectance spectrophotometer from the topsheet side of the product 1. Preferably, in certain embodiments, the color difference delta E is at least 50% less, such as at least 60% less. In this way, a visual impression of the product can be further improved and the visibility of the elastic elements is decreased and the elastic elements are sufficiently masked.

Alternatively or additionally, the color difference delta E and/or delta L*-value between the printed pattern 800 in the edge area 8 free from elastic elements 10, 10' and a printed pattern free area 610 of the topsheet 2 covering the core 6, measured as described above from the topsheet side of the product 1, is at least 10, such as at least 15. In this way the contrast between the printed areas and the non-printed areas is visible, and thus the visual appearance of the hygiene product is improved.

The colored pattern may be applied on the topsheet material by any printing means commonly known in the art, such as by means of non-contact printing, for example ink-jet printing, or contact printing, for example gravure printing, flexographic printing, lithographic printing including offset printing and screen printing, or by combinations of different printing methods. For example, one part of the colored pattern may be applied by contact printing, and another part of the pattern may be applied by non-contact printing. The pattern may be provided on the surface of said topsheet facing away from said backsheet, or on the surface of said topsheet facing said back sheet, or alternatively, part of the pattern may be provided on the surface of said topsheet facing away from said backsheet while part of the pattern is provided on the surface of said topsheet facing said backsheet.

Suitably, the colored pattern is repetitive along a longitudinal extension of said absorbent product in a printing direction. Suitably, the repeating unit length is longer than the maximum length of the absorbent product along said longitudinal extension or, the pattern may be repetitive in a direction along a transverse extension of said absorbent product, having a repeating unit longer than the maximum width of the absorbent product along said longitudinal extension. The printing direction is typically parallel to the machine direction in which the products are produced, and may for example be substantially parallel to the longitudinal or transversal extension of said absorbent product, having a repeating unit length of less than or equal to the maximum length of the absorbent product along said longitudinal extension or transversal extension, respectively. The length of the repeating unit may for example be in the range of from 5-80 cm, depending on the type of the absorbent product.

In embodiments of the absorbent hygiene product, the color of that surface of the backsheet that faces away from the topsheet, i.e. on the back-side of the product, exhibits a color that is close to that of the color of the areas which are free of the elastic elements in the edge area 8.

The shape of the absorbent product may be substantially triangular or resemble a triangular shape, substantially quadrilateral or resemble quadrilateral shape, or it may resemble an hourglass-shape. Each of FIG. 1-3 illustrates a product having a triangular, tapered shape. FIG. 1 illustrates different portions of the product, which are also applicable in FIGS. 2 and 3. The product has a wider head portion b1 and a narrower intermediate portion b2 and a rear portion b3. The head portion b1 may constitute about 5-25% of the longitudinal extension of the product, the intermediate portion b2 about 60-90% and the rear portion about 5-15%. As illustrated in FIGS. 2 and 3, the centre line A divides the product 1 into mirror imaged first and second longitudinal portions I; II which are symmetrical in respect of the centre line A. However, according to some embodiments, the product does not need to be symmetrical in respect of the centre line A. The product comprises in each longitudinal portion I; II an arch-shaped edge portion 12; 12' having two opposing outermost first transition points T1; T1' in the transverse direction in the outermost edge 80 of the edge portion 8. The product has its broadest product width between the first transition points T1; T1', i.e. the broadest first product width extends transversally between said outermost first transition points T1; T1'. The head portion b1 transitions into the intermediate product portion b2 at said first transition points T1; T1', as illustrated by the line extending between the first transition points T1; T1'. The edge portion 8 in the intermediate product portion b2 tapers towards a central end point T10 in the rear portion b3 of the product. The intermediate portion b2 transitions to the rear portion b3 at rear portion transition points T2; T2' which are longitudinally distanced from the first transition points T1; T1' and the central end point T10.

The elastic elements usually extend in the first and second longitudinal portions (I; II) in the intermediate portion b2 whatever the shape of the product. It can be seen from the embodiments shown in FIG. 1-3 that the elastic elements 10; 10' extend in the edge area 8 in the first and second longitudinal portions I; II within the intermediate rear portion b2 and are inclined in respect of the centre line A. The inclination follows the tapering angle of the edge area 8, so that a comfortable product is provided. In this way it is possible to provide a bowl shape to the product and thus optimal fit. The shape of the product could be resembling an hourglass-shape (not shown) comprising a head portion, a centrally located intermediate portion and a rear portion. In such products the elastic elements can also extend in the first and second longitudinal portions in the intermediate portion.

The present invention further relates to a process for the production of a disposable hygiene product and comprises the steps of first providing a layer of topsheet material, a layer of backsheet material and an absorbent material for an absorbent core and forming the core.

The core can be formed for example by means of matforming through an air-laying process. In the process an air-permeable mould is provided. Fibrous material is air-laid into the mould and the mould is filled, whereby an absorbent core is produced in with a desired amount of fibrous material. The process also includes providing a material for elastic elements. The elastic elements are suitably provided as rolled up material and they are fed to the process in a pre-tensioned condition. The elastic elements are fed such that they are arranged between the layer of the topsheet material and the backsheet material. Before attaching the layers by means of an adhesive, the elastic elements are cut to a predetermined length and positioned at a correct position in the product. The positioning of the elastic elements is adapted to the absorbent core, which is also fed between the topsheet layer and the backsheet layer. The topsheet layer, the backsheet layer and the elastic elements are attached together along the peripheral edge area of the product by means of attachment means, preferably adhesive, in an embodiment. The topsheet may be pre-printed or it may be printed online with the product assembly line. The printed pattern is synchronized with the placement of the absorbent core and the printed pattern 800 is arranged such that it masks the elastic elements.

EXAMPLES

Figure 5:
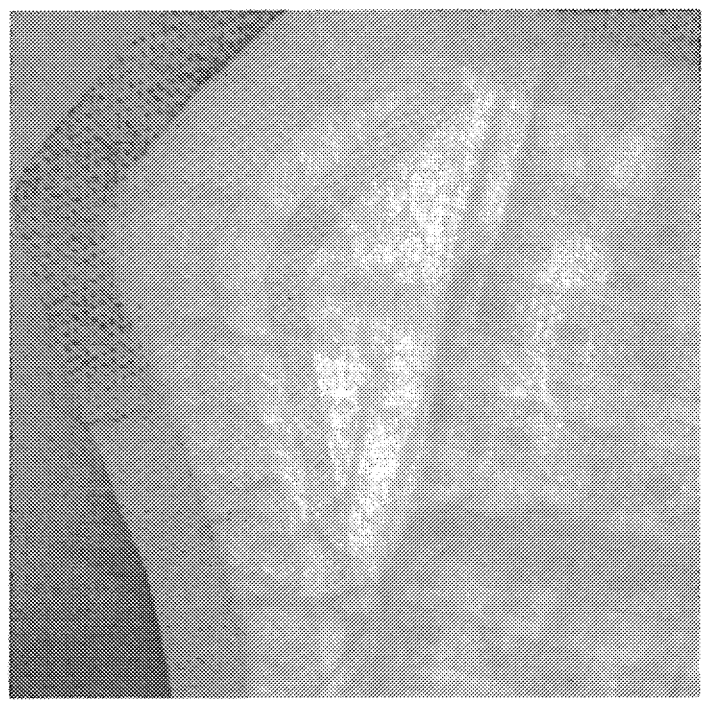
FIG. 5 shows a photograph of a portion of an absorbent product provided with a printed pattern which masks the elastic elements.

Color measurements according to the above-mentioned method was performed on two different incontinence pads essentially as depicted in FIG. 5 with a colored backsheet and bands of white foam elastics constituting the elastic elements. The pads were identical apart from the color of the print pattern on the topsheet.

The reported values are each the average value of 10 measurements.

The measurements were taken at the following positions on the product:

A) in a part of the edge area comprising elastic elements

B) in a part of the edge area not comprising elastic elements

C) on a non-printed area inside the core perimeter

Delta E between A and B and A and C values were calculated for each one of the pads with the following results:

|  | Pad 1 | Pad 2 |
| --- | --- | --- |
| $\Delta E_{A-B}$ | 9.2 | 8.5 |
| $\Delta E_{A-C}$ | 24.3 | 35.7 |

As can be seen, the color difference deltaE is, consistently lower between the areas A and B, i.e. between a part of the edge area comprising elastic elements and a part of the edge area not comprising elastic elements, than between the areas A and C, i.e. between a part of the edge area comprising elastic elements and a non-printed area inside the core perimeter Although the above discussion has been exemplified through a male incontinence pad or guard, the present invention is also applicable to other absorbent products such as diapers, female incontinence pads, sanitary napkins or panty-liners. For instance, application of the invention to diapers would provide similar benefits in terms of comfort, fit and leakage-prevention.

The invention should not be considered as limited by the above description; rather the scope and limitations of the invention are defined by the enclosed claims.

The invention claimed is:

1. A disposable hygiene absorbent product comprising a liquid-permeable topsheet of a translucent material, a liquid-impermeable backsheet and an absorbent core arranged between the topsheet and the backsheet, wherein the absorbent product has a longitudinally extending centre line (A) extending centrally through the absorbent product, wherein the absorbent product extends, in a flattened-out configuration, in a longitudinal direction (Y) and in a transversal direction (X) and wherein the topsheet and the backsheet have extensions in the longitudinal and the transversal directions and the topsheet and the backsheet have substantially the same extensions in the longitudinal and the transversal directions and the absorbent core has a smaller extension than the topsheet and the backsheet in both the longitudinal and the transversal directions, the core being surrounded with a peripheral edge area which comprises the topsheet and the backsheet, wherein the edge area comprises over at least a portion of the length on each respective side of the centre line (A) an elastic element extending longitudinally in the direction following the shape of the core and/or an outermost peripheral edge of the edge area, wherein the backsheet has a different inherent color than inherent colors of the topsheet, the core and the elastic elements, and has a lower L*-value than L*-values of the topsheet, the core and the elastic elements measured by a reflectance spectrophotometer, and the topsheet is provided with a printed pattern arranged to mask the elastic elements, wherein the printed pattern covers the elastic elements and areas free of the elastic elements in the peripheral edge area, and wherein the printed pattern extends symmetrically from the outermost peripheral edge of the edge area towards a centre point (C) of the product over a core edge such that at least 50% of the total area of the topsheet covering the core is free of the printed pattern.

2. The disposable hygiene absorbent product according to claim 1, wherein a color difference delta E between the printed pattern in the edge area comprising the elastic elements and the printed pattern in the edge area free of the elastic elements is less than 10, measured by means of a reflectance spectrophotometer from the topsheet side of the product.

3. The disposable hygiene absorbent product according to claim 1, wherein a color difference delta E between the printed pattern in the edge area comprising the elastic elements and the printed pattern in the edge area free of elastic elements is less than a color difference delta E between the printed pattern in the edge area comprising the elastic elements and a printed pattern free area of the topsheet covering the core, measured by means of a reflectance spectrophotometer from the topsheet side of the product.

4. The disposable hygiene absorbent product according to claim 1, wherein a difference delta E and/or a delta L*-value between the printed pattern in the edge area free from elastic elements and a printed pattern free area of the topsheet covering the core, measured by means of a reflectance spectrophotometer from the topsheet side of the product, is at least 10.

5. The disposable hygiene absorbent product according to claim 1, wherein the printed pattern comprises a pattern having the same color but different chroma and/or lightness than the backsheet.

6. The disposable hygiene absorbent product according to claim 1, wherein the printed pattern comprises pattern having different color, chroma and/or lightness than the backsheet.

7. The disposable hygiene absorbent product according to claim 1, wherein the backsheet, topsheet and elastic elements arranged between the topsheet and the backsheet are joined together along the edge area by means of adhesive.

8. The disposable hygiene product according to claim 1, wherein the centre line (A) divides the product into mirror imaged first and second longitudinal portions which are symmetrical in respect of the centre line (A).

9. The disposable hygiene product according to claim 8, wherein the product has a head portion, an intermediate portion and a rear portion, wherein the head portion comprises in each longitudinal portion an arch-shaped edge portion having two opposing outermost first transition points in the transverse direction in the outermost edge of the edge portion, wherein a broadest first product width extends between said outermost first transition points and wherein the head portion transitions into the intermediate product portion at said first transition points, the edge portion in the intermediate product portion tapering towards a central end point in the rear portion of the product, wherein the intermediate portion transitions to the rear portion at rear portion transition points longitudinally distanced from the first transition points and the central end point.

10. The disposable hygiene product according to claim 9, wherein the shape of the product resembles a triangular shape.

11. The disposable hygiene product of claim 10, wherein the elastic elements extend in the edge area in the first and second longitudinal portions within the intermediate rear portion and are inclined in respect of the centre line.

12. The disposable hygiene product according to claim 1, wherein the shape of the product resembles a quadrilateral shape.

13. The disposable hygiene product according to the preceding claim 1, wherein the shape of the product resembles an hourglass-shape, and wherein the product comprises a head portion, a centrally located intermediate portion and a rear portion, wherein the elastic elements extend in first and second longitudinal portions in the intermediate portion.

14. The disposable hygiene product according to claim 1, wherein the elastic elements comprise foam elastics or laminate film elastics.

15. The disposable hygiene product according to claim 1, wherein the topsheet comprises a further printed pattern distanced from the printed pattern arranged to mask the elastic elements.

16. The disposable hygiene absorbent product according to claim 1, wherein the printed pattern additionally covers at least a core peripheral portion covering a core edge.

17. The disposable hygiene absorbent product according to claim 1, wherein a color difference delta E between the printed pattern in the edge area comprising the elastic elements and the printed pattern in the edge area free of elastic elements is at least 50% less than a color difference delta E between the printed pattern in the edge area comprising the elastic elements and a printed pattern free area of the topsheet covering the core, measured by means of a reflectance spectrophotometer from the topsheet side of the product.

\* \* \* \* \*